United States Patent
Sawada et al.

(10) Patent No.: US 6,761,895 B2
(45) Date of Patent: Jul. 13, 2004

(54) DRUG DELIVERY SYSTEM FOR AVERTING PHARMACOKINETIC DRUG INTERACTION AND METHOD THEREOF

(75) Inventors: Toyohiro Sawada, Shizuoka (JP); Kazuhiro Sako, Shizuoka (JP); Tatsunobu Yoshioka, Shizuoka (JP); Shunsuke Watanabe, Shizuoka (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/834,414

(22) Filed: Apr. 12, 2001

(65) Prior Publication Data

US 2002/0022054 A1 Feb. 21, 2002

Related U.S. Application Data

(60) Provisional application No. 60/197,574, filed on Apr. 17, 2000.

(51) Int. Cl.⁷ .................................................. A61K 9/00
(52) U.S. Cl. ........................................................ 424/400
(58) Field of Search ......................................... 424/468

(56) References Cited

U.S. PATENT DOCUMENTS 4,891,223 A * 1/1990 Ambegaonkar et al. .... 424/408

FOREIGN PATENT DOCUMENTS

| EP | 0 823 255 | 11/1998 |
|----|-----------|---------|
| JP | 60-193917 | 2/1995 |

OTHER PUBLICATIONS

Yasufumi Sawada, et al., *Yakuzal Yosokugaku Nyuumon; Byouin Yakuzaishi to Yosokugaku* (3). Gekkan Yakuji (1991). vol. 33, No. 7, pp. 84–93.

Koilchi Kitada, *Yakubutsu Taisha Kouso (especially, p. 450) no Sogai ni kansuru Sougo Sayou no Kiso Chishiki*, Gekkan Yakuji (1996), vol. 38, No. 3, pp. 47–59.

Eml Nakajima, et al., *Yakubutsu Taisha Kouso no Yuudou ni kansuru Sougo Sayou no Koso Chishiki*, Gekkan Yakuji (1996), vol. 38, No. 3, pp. 62–68.

Ikumi Tamal, *Yakubutsu Kyuushuu ni kansuru Sougo Sayou no Kiso Chishiki*, Gekkan Yakuji (1996), vol. 38, No. 3, pp. 69–78.

* cited by examiner

*Primary Examiner*—Shelley A. Dodson
*Assistant Examiner*—Konata M. George
(74) *Attorney, Agent, or Firm*—Townsend and Townsend and Crew LLP

(57) ABSTRACT

The present invention is a system for averting undesirable pharmacokinetic drug interaction between a drug and concomitant drug(s), which consists of controlling the in vivo release time and/or release site of the drug and/or the concomitant drug.

16 Claims, 1 Drawing Sheet

DRUG DELIVERY SYSTEM FOR AVERTING PHARMACOKINETIC DRUG INTERACTION AND METHOD THEREOF

CROSS-REFERENCE TO RELATED APPLICATIONS

The present application claims priority to U.S. Provisional Application No. 60/197,574, filed Apr. 17, 2000, the teaching of which is hereby incorporated by reference in its entirety for all purposes.

TECHNICAL FIELD

The present invention pertains to a novel means for averting undesirable pharmacokinetic (drug) interaction between a drug and concomitant drug(s) (e.g., between a drug and a food) in vivo in humans, and uses as the means of aversion a drug delivery system with which the in vivo release time and/or the release site of the drug is controlled.

BACKGROUND OF THE INVENTION

Recently, drugs are rarely used singularly as a result of diversification of medicine and changes in patient phase with aging, and in many cases multiple drugs are administered simultaneously or at staggered administration times. In this case, interaction between drugs that are administered concomitantly sometimes occurs. Interaction between the drugs in question is classified as pharmacodynamic drug interaction, whereby there is a change in sensitivity, etc., to the drug at its site of action, and pharmacokinetic drug interaction, where there is a change in the in vivo kinetics of the drug. With respect to the former, interaction by concomitant use can be estimated if the clinical mode of action of the drugs is known, and the fact of the matter is that the actual results of concomitant therapy are improved using this same interaction. However, with respect to the latter, clinically, the in vivo kinetics of a drug is still unknown and even when it is known, unexpected results occur when drugs are combined ("Clinical Pharmacokinetics, Revised Version 2," Chapter VII: Drug Interaction, page 107, Ryuichi Kato, author, Nankodo Publishing).

Pharmacokinetic drug interaction almost always develops because the drugs themselves compete for one route (enzymes, carriers, etc.) when drugs that use the same routes in terms of drugs absorption, distribution, metabolism or excretion are used concomitantly.

This type of pharmacokinetic drug interaction is undesirable unless it is used for an additive action or synergism. The method has been adopted for averting concomitant use of drugs that interact with one another when a prescription is written by a physician or pharmacist whereby attention is drawn to "Drug Safety Data" presented by the Ministry of Health and Welfare and the column on precautions for concomitant use contained in the attached drug literature.

Moreover, the claim is presented in "Yakuzai Yosokugaku Nyumon," (Yasufumi Sawada, author; Yakugyo Jiho Publishers) that it is possible to avert interaction with an administration protocol whereby the administration time of concomitant drugs to a patient is staggered. However, the administration time is precisely specified and the protocol calls for administration of as much as 6 to 7 times/day with concomitant use of metal cation-containing antacids (magnesium, aluminum, etc.) and new quinolones (norfloxacin, etc.), which were used as examples in this text, and in view of patient compliance, this protocol cannot realistically be used.

Consequently, even if from a pharmacological standpoint the drugs themselves realize excellent therapeutic results when used concomitantly, concomitant use has been averted in the past because of drug interaction and satisfactory therapeutic results could not be realized.

Moreover, since pharmacokinetic interaction with drugs is induced by some foods, pharmacists give instructions on how to take drugs explaining precautions when drugs are taken. However, this has become a source of reduced patient compliance.

SUMMARY OF THE INVENTION

In certain embodiments, the present invention provides a system for averting undesirable pharmacokinetic drug interaction between a drug and concomitant drug(s), the system comprising controlling the in vivo release time and/or release site of the drug and/or the concomitant drug(s).

In another embodiment, the present invention provides a method or use of a drug delivery system which consists of controlling the in vivo release time and/or release site a drug and/or concomitant drug(s), for averting undesirable pharmacokinetic drug interaction between the drug and the concomitant drug(s).

In another embodiment, the present invention provides a method or use of a drug delivery system which consists of controlling the in vivo release time and/or release site of the drug and/or concomitant drug(s), for averting undesirable drug interaction between the drug and the concomitant drug(s), both of which use the same route in terms of in vivo drug absorption, distribution, metabolism or excretion in humans.

In another embodiment, the present invention provides a method or use of a drug delivery system which consists of timed-release control of a drug or control of the site of release of a drug to the digestive tract, for averting undesirable drug interaction between the said drug and concomitant drug(s), both of which are metabolized by the same molecular species of drug-metabolizing enzyme in humans, or between the said drug and concomitant drug(s) that is metabolized by the molecular species of drug-metabolizing enzymes that is inhibited by the said drug.

In another embodiment, the present invention provides a method or use of a drug delivery system which consists of timed-release control of a drug or control of release of a drug specifically to the lower digestive tract, for averting undesirable drug interaction between the said drug and concomitant drug(s), both of which metabolized by the drug metabolizing enzyme CYP3A4, or between the said drug that inhibit CYP3A4 and concomitant drug(s) that is metabolized by CYP3A4.

In another embodiment, the present invention provides a method of averting undesirable pharmacokinetic drug interaction between a drug and concomitant drug(s), by using a drug delivery system with which the in vivo release time and/or release site of the drug and/or the concomitant drug(s) is controlled.

In another embodiment, the present invention provides a method for averting undesirable drug interaction between a drug and concomitant drug(s), both of which use the same route in terms of in vivo drug absorption, distribution, metabolism or excretion in humans, by using a drug delivery system with which the in vivo release time and/or release site of the drug and/or the concomitant drug(s) is controlled.

In another embodiment, the present invention provides a method for averting undesirable drug interaction between a drug and concomitant drug(s), both of which are metabolized by the same molecular species of drug-metabolizing enzyme in humans or between a drug and concomitant drug(s) that is metabolized by the molecular species of drug metabolizing-enzymes that is inhibited by the said drug, by using a drug delivery system with which there is timed-release control of the said drug or control of the site of release of the said drug to the digestive tract.

In another embodiment, the present invention provides a method for averting undesirable drug interaction between a drug and concomitant drug(s), both of which metabolized by the drug metabolizing enzyme CYP3A4 or between a drug that inhibit CYP3A4 and concomitant drug that is metabolized by CYP3A4, by using a drug delivery system with which there is timed-release control of the said drug or control of release of the said drug specifically to the lower digestive tract.

In still another embodiment, the present invention provides a method or use of a drug preparation which consists of controlling the in vivo release time and/or release site of a drug, for averting undesirable pharmacokinetic drug interaction between the said drug and concomitant drug(s).

In still another embodiment, the present invention provides a method or use of a drug preparation which consists of controlling the in vivo release time and/or release site of a drug, for averting undesirable drug interaction between the said drug and concomitant drug(s), both of which use the same route in terms of in vivo drug absorption, distribution, metabolism or excretion in humans.

In another embodiment, the present invention provides a method or use of a drug preparation which consists of timed-release control of a drug or control of the site of release of a drug to the digestive tract is controllable, for averting undesirable drug interaction on the in vivo kinetics of concomitant drug(s) by the said drug that inhibits the in vivo metabolism of the concomitant drug(s) by drug-metabolizing enzymes in humans.

In another embodiment, the present invention provides a method or use of a drug preparation which consists of timed-release control of a drug or control of release of a drug specifically to the lower digestive tract, for averting undesirable effects on the blood concentration of concomitant drug(s) by the said drug that inhibits the in vivo metabolism of the concomitant drug(s) by CYP3A4 in humans. Preferably, the drug and the concomitant drug are a combination selected from anfentanyl, fentanyl, sulfentanyl, cocaine, dihydrocodeine, oxycodeine, tramadol, erythromycin, clarithromycin, troleandomycin, azithromycin, itraconazole, ketoconazole, dapsone, midazolam, triazolam, alprazolam, diazepam, zolpidem, felodipine, nifedipine, nitrendipine, amlodipine, isradipine, nicardipine, nimodipine, nisoldipine, nildipine, bepridil, diltiazem, verapamil, astemizole, terfenadine, loratidine, cyclosporine, tacrolimus, rapamycin, amiodarone, disopyramide, lidocaine, propafenone, quinidine, imipramine, amitriptyline, clomipramine, nafazodone, sertraline, trazodone, haloperidol, pimozide, carbamazepine, ethosuximide, trimethadione, simvastatin, lovastatin, fluvastatin, atrovastatin, etoposide, ifosfamide, paclitaxel, tamoxifen, taxol, vinblastine, vincristine, indinavir, ritonavir, saquinavir, testosterone, prednisolone, methylprednisolone, dexamethasone, proguanil, warfarin, finasteride, flutamide, ondansteron, zatsetrone, cisapride, cortisol, zonisamide, desmethyldiazepam, and conivaptan.

In still yet another embodiment, the present invention provides a method or use of a drug delivery system which consists of controlling the in vivo release time and/or release site a drug, for averting undesirable pharmacokinetic interaction between the drug and food(s).

In still yet another embodiment, the present invention provides a method for averting undesirable pharmacokinetic interaction between a drug and food(s), by using a drug delivery system whereby the in vivo release time and/or release site of the drug is controlled.

These and other embodiments will become more apparent when read with the detailed description and drawings, which follow.

DETAILED DESCRIPTION OF THE INVENTION AND PREFERRED EMBODIMENTS

Figure 1:
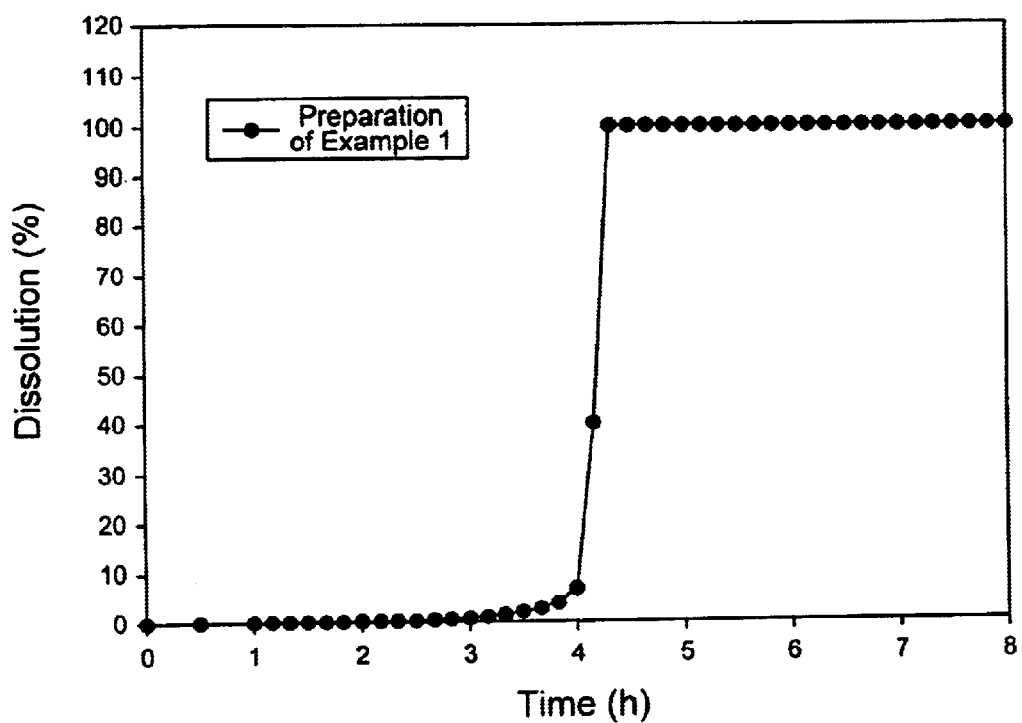
FIG. 1 shows the results of dissolution tests of conivaptan timed-release preparation.

The inventors focused on the use of a drug delivery system for averting undesirable drug interaction, particularly pharmacokinetic drug interaction, and were successful at materialization of the same. They discovered that with respect to drug interaction that is produced as a result of the drugs themselves competing for one route (enzyme, carrier, etc.) when multiple drugs that use the same route in terms of drug absorption, distribution, metabolism or excretion are administered concomitantly, drug interaction at the route that is the problem can be averted by controlling the drug release time and/or release site with a drug delivery system. Furthermore, not only drug interaction between multiple drugs, but also interaction between drugs and foods, can be similarly averted.

A version of drug interaction as a purpose and use of the technology in question has not been specifically discussed in the technical field of drug delivery systems.

That is, the present invention pertains to a system for averting undesirable pharmacokinetic drug interaction between a drug and concomitant drug(s), which consists of controlling the in vivo release time and/or release site of the drug and/or the concomitant drug(s). In particular, the present invention pertains to a system for averting undesirable drug interaction between a drug and concomitant drug (s), both of which use the same route in terms of in vivo drug absorption, distribution, metabolism or excretion in humans, which consists of controlling the in vivo release time and/or release site of the drug and/or the concomitant drug(s). The present invention is preferably a system for averting undesirable drug interaction between a drug and concomitant drug(s), both of which are metabolized by the same molecular species of drug-metabolizing enzyme in humans or between a drug and concomitant drug(s) that is metabolized by the molecular species of drug-metabolizing enzymes that is inhibited by the said drug, which consists of timed-release control of the said drug or control of the site of release of the said drug to the digestive tract. It is further preferred that the present invention is a system for averting undesirable drug interaction between a drug and concomitant drug(s), both of which metabolized by the drug metabolizing enzyme CYP3A4, or between a drug that inhibits CYP3A4 and concomitant drug(s) that is metabolized by CYP3A4, which consists of timed-release control of the said drug or controlling release specifically in the lower digestive tract of the said drug.

Moreover, the present invention pertains to the use of a drug delivery system which consists of controlling the in vivo release time and/or release site a drug and/or concomitant drug(s), for averting undesirable pharmacokinetic drug interaction between the drug and the concomitant drug(s). In particular, the present invention pertains to the use of a drug delivery system which consists of controlling the in vivo release time and/or release site of the drug and/or concomitant drug(s), for averting undesirable drug interaction between the drug and the concomitant drug(s), both of which use the same route in terms of in vivo drug absorption, distribution, metabolism or excretion in humans. The present invention preferably is the use of a drug delivery system which consists of timed-release control of a drug or control of the site of release of a drug to the digestive tract, for averting undesirable drug interaction between the said drug and concomitant drug(s), both of which are metabolized by the same molecular species of drug-metabolizing enzyme in humans, or between the said drug and concomitant drug(s) that is metabolized by the molecular species of drug-metabolizing enzymes that is inhibited by the said drug. It is further preferred that the present invention is the use of a drug delivery system which consists of timed-release control of a drug or control of release of a drug specifically to the lower digestive tract, for averting undesirable drug interaction between the said drug and concomitant drug(s), both of which metabolized by the drug metabolizing enzyme CYP3A4, or between the said drug that inhibit CYP3A4 and concomitant drug(s) that is metabolized by CYP3A4.

Moreover, the present invention pertains to a method for averting undesirable pharmacokinetic drug interaction between a drug and concomitant drug(s), by using a drug delivery system whereby the in vivo release time and/or release site of the drug and/or the concomitant drug(s) is controlled. In particular, the present invention pertains to a method for averting undesirable drug interaction between a drug and concomitant drug(s), both of which use the same route in terms of in vivo drug absorption, distribution, metabolism or excretion in humans, by using a drug delivery system with which the in vivo release time and/or release site of the drug and/or the concomitant drug(s) is controlled. The present invention is preferably a method for averting undesirable drug interaction between a drug and concomitant drug(s), both of which are metabolized by the same molecular species of drug-metabolizing enzyme in humans or between a drug and concomitant drug(s) that is metabolized by the molecular species of drug metabolizing-enzymes that is inhibited by the said drug, by using a drug delivery system with which there is timed-release control of the said drug or control of the site of release of the said drug to the digestive tract. It is further preferred that the present invention is a method for averting undesirable drug interaction between a drug and concomitant drug(s), both of which metabolized by the drug metabolizing enzyme CYP3A4 or between a drug that inhibits CYP3A4 and concomitant drug(s) that is metabolized by CYP3A4, by using a drug delivery system with which there is timed-release control of the said drug or control of release of the said drug specifically to the lower digestive tract.

The present invention further pertains to a drug preparation for averting undesirable pharmacokinetic drug interaction between a drug and concomitant drug(s), which consists of controlling the in vivo release time and/or release site of the said drug. In particular, the present invention pertains to a drug preparation for averting undesirable drug interaction between a drug and concomitant drug(s), both of which use the same route in terms of in vivo drug absorption, distribution, metabolism or excretion in humans, which consists of controlling the in vivo release time and/or release site of the said drug. The present invention is preferably a drug preparation for averting undesirable drug interaction on the in vivo kinetics of a drug by concomitant drug(s) that inhibits in vivo metabolism of the said drug in humans, which consists of timed-release control of the concomitant drug(s) or control of the site of release of the concomitant drug(s) to the digestive tract. It is further preferred that the present invention is a drug preparation for averting undesirable effects on the blood concentration of a drug by concomitant drug(s) that inhibits the in vivo metabolism of the said drug by CYP3A4 in humans, which consists of timed release control of the said drug or controlling release specifically in the lower digestive tract of the concomitant drug(s).

Moreover, the present invention pertains to the use of a drug preparation which consists of controlling the in vivo release time and/or release site of a drug, for averting undesirable pharmacokinetic drug interaction between the said drug and concomitant drug(s). In other words, the present invention pertains to a drug preparation which consists of controlling the in vivo release time and/or release site of a drug, for averting undesirable drug interaction between the said drug and concomitant drug(s), both of which use the same route in terms of in vivo drug absorption, distribution, metabolism or excretion in humans. The present invention is preferably the use of a drug preparation which consists of timed-release control of a drug or control of the site of release of a drug to the digestive tract, for averting undesirable drug interaction on the in vivo kinetics of concomitant drug(s) by the said drug that inhibits the in vivo metabolism of the concomitant drug(s) by drug-metabolizing enzymes in humans. It is further preferred that the present invention is the use of a drug preparation which consists of timed-release control of a drug or control of release of a drug specifically to the lower digestive tract, for averting undesirable effects on the blood concentration of concomitant drug(s) by the said drug that inhibits the in vivo metabolism of the concomitant drug(s) by CYP3A4 in humans.

Furthermore, the present invention pertains to a method for averting undesirable pharmacokinetic drug interaction between a drug and concomitant drug(s), which comprises administering to patients a drug preparation with which the in vivo release time and/or release site of the said drug is controlled. In particular, the present invention pertains to a method for averting undesirable drug-interaction between a drug and concomitant drug(s), both of which use the same route in terms of in vivo drug absorption, distribution, metabolism or excretion in humans, which comprises administering to patients a drug preparation with which the in vivo release time and/or release site of the said drug is controllable. The present invention is preferably a method for averting undesirable drug-interaction on the in vivo kinetics of a drug by a concomitant drug that inhibits the in vivo metabolism of the said drug by drug-metabolizing enzymes in humans, which comprises administering to patients a drug preparation with which timed-release of the concomitant drug or release site of the concomitant drug to the digestive tract is controllable. It is further preferred that the present invention is a method for averting undesirable effects on the blood concentration of a drug by a concomitant drug that inhibits the in vivo metabolism of the said drug by CYP3A4, which comprises administering to patients a drug preparation with which timed-release of the concomitant drug or release of the concomitant drug specifically to the lower digestive tract is controllable.

Moreover, the present invention pertains to a system for averting undesirable pharmacokinetic interaction between a drug and food(s), which consists of controlling the in vivo release time and/or release site of the drug. In particular, the present invention pertains to a system for averting undesirable pharmacokinetic interaction between a drug and food (s), both of which use the same route in terms of in vivo drug absorption, distribution, metabolism or excretion in humans, which consists of controlling the in vivo release time and/or release site of the drug. The present invention is preferably a system for averting undesirable pharmacokinetic interaction between a drug and food(s), both of which are metabolized by the same molecular species of drug-metabolizing enzyme in humans, or between a drug and food(s) that inhibit the molecular species of drug metabolizing enzymes that metabolize the said drug, which consists of timed-release control of the said drug or control of the site of release of the said drug to the digestive tract. It is further preferred that the present invention is a system for averting undesirable pharmacokinetic interaction between a drug and food(s), both of which metabolized by the drug-metabolizing enzyme CYP3A4, or between a drug that is metabolized by CYP3A4 and food(s) that inhibit CYP3A4, which consists of timed release control or controlling release specifically in the lower digestive tract of the said drug.

In addition, the present invention pertains to the use of a drug delivery system which consists of controlling the in vivo release time and/or release site of a drug, for averting undesirable pharmacokinetic interaction between the drug and food(s). In particular, the present invention pertains to the use of a drug delivery system which consists of controlling the in vivo release time and/or release site of a drug, for averting undesirable pharmacokinetic interaction between the drug and food(s), both of which use the same route in terms of in vivo drug absorption, distribution, metabolism or excretion in humans. The present invention preferably is the use of a drug delivery system which consists of timed-release control of a drug or control of the site of release of a drug to the digestive tract, for averting undesirable pharmacokinetic interaction between the drug and food(s), both of which are metabolized by the same molecular species of drug metabolizing enzyme in humans or between the drug and food(s) that inhibits the molecular species of drug-metabolizing enzymes that metabolize the said drug. It is further preferred that the present invention is the use of a drug delivery system which consists of timed-release control of a drug or control of release of a drug specifically to the lower digestive tract, for averting undesirable pharmacokinetic interaction between the drug and food(s), both of which metabolized by the drug metabolizing enzyme CYP3A4, or between the drug that are metabolized by CYP3A4 and food(s) that inhibits CYP3A4.

Furthermore, the present invention pertains to a method for averting undesirable pharmacokinetic interaction between a drug and food(s), by using a drug delivery system whereby the in vivo release time and/or release site of the drug is controlled. In particular, the present invention pertains to a method for averting undesirable pharmacokinetic interaction between a drug and food(s), both of which use the same route in terms of in vivo drug absorption, distribution, metabolism or excretion in humans by using a drug delivery system with which the in vivo release time and/or release site of drugs is controlled. The present invention is preferably a method for averting undesirable pharmacokinetic interaction between a drug and food(s), both of which are metabolized by the same molecular species of drug-metabolizing enzyme in humans or between a drug and food(s) that inhibits the molecular species of drug metabolizing enzymes that metabolize the said drug, by using a drug delivery system with which there is timed-release control of the drug or control of the site of release of the drug to the digestive tract. It is further preferred that the present invention is a method for averting undesirable pharmacokinetic interaction between a drug and food(s), both of which metabolized by the drug-metabolizing enzyme CYP3A4 or between a drug that are metabolized by CYP3A4 and food(s) that inhibits CYP3A4, by using a drug delivery system with which there is timed-release control of the drug or control of release of the drug specifically to the lower digestive tract.

Furthermore, the present invention pertains to a drug preparation for averting undesirable pharmacokinetic interaction between a drug and food(s), which consists of controlling the in vivo release time and/or release site of the drug. In particular, the present invention pertains to a drug preparation for averting undesirable pharmacokinetic interaction between a drug and food(s), both of which use the same route in terms of in vivo drug absorption, distribution, metabolism or excretion in humans, which consists of controlling the in vivo release time and/or release site of the drug. The present invention is preferably a drug preparation for averting undesirable pharmacokinetic interaction on the in vivo kinetics of a drug by food(s) that inhibits in vivo metabolism of the drug in humans, which consists of timed-release control of the drug or control of the site of release of the drug to the digestive tract. It is further preferred that the present invention is a drug preparation for averting undesirable effects on the blood concentration of a drug by food(s) that inhibits the in vivo metabolism of the drug by CYP3A4 in humans, which consists of timed-release control of the drug or controlling release specifically to the lower digestive tract of the drug.

Moreover, the present invention pertains to the use of a drug preparation which consists of controlling the in vivo release time and/or release site of a drug, for averting undesirable pharmacokinetic interaction between the drug and food(s). In other words, the present invention pertains to the use of a drug preparation which consists of controlling the in vivo release time and/or release site of a drug, for averting undesirable pharmacokinetic interaction between a drug and food(s), both of which use the same route in terms of in vivo drug absorption, distribution, metabolism or excretion in humans. The present invention is preferably the use of a drug preparation which consists of timed-release control of a drug or control of the site of release of a drug to the digestive tract, for averting undesirable pharmacokinetic interaction on the in vivo kinetics of the drug by food(s) that inhibit the in vivo metabolism in humans of the drug by drug-metabolizing enzymes. It is further preferred that the present invention is the use of a drug preparation which consists of timed-release control of a drug or control of release of a drug specifically to the lower digestive tract, for averting undesirable effects on the blood concentration of the drug by food(s) that inhibits in vivo metabolism of the drug by CYP3A4 in humans.

Furthermore, the present invention pertains to a method for averting undesirable pharmacokinetic interaction between a drug and food(s), which comprises administering to patients a drug preparation with which the in vivo release time and/or release site of the drug is controlled. In particular, the present invention pertains to a method for averting undesirable pharmacokinetic interaction between a drug and food(s), both of which use the same route in terms of in vivo drug absorption, distribution, metabolism or excretion in humans, which comprises administering to patients a drug preparation with which the in vivo release time and/or release site of the drug is controllable. The present invention is preferably a method for averting undesirable interaction on the in vivo kinetics of a drug by food(s) that inhibits the in vivo metabolism of the drug by drug-metabolizing enzymes in humans, which comprises administering to patients a drug preparation with which timed-release of the drug or release site of the drug to the digestive tract is controllable. It is further preferred that the present invention is a method for averting undesirable effects on the blood concentration of a drug by food(s) that inhibits in vivo metabolism of the drug by CYP3A4, which comprises administering to patients a drug preparation with which timed-release of the drug or release of the drug specifically to the lower digestive tract is controllable.

The present invention will now be explained in further detail.

In the present invention the term drug interaction means pharmacokinetic drug interaction, in other words, drug interaction between multiple drugs that use the same route in terms of (a)drug metabolism, (b)drug absorption, (c)drug distribution, or (d)drug excretion. Specific interaction is discussed below:

(a) Interaction in terms of drug metabolism

Drugs are deactivated or converted to water-soluble metabolites that are readily excreted via the kidneys by the effects of drug-metabolizing enzymes in the liver. Cytochrome P450 (CYP) is said to be the most important drug-metabolizing enzyme. It is said that approximately 70% of pharmacokinetic drug interaction is around drug metabolism, and of this, 95% or more is interaction via CYP. Many molecular species of CYP exist, and those that play the most important role in drug metabolism are CYP1A2, CYP2C9, CYP2C19, CYP2D6 and CYP3A4. The molecular species of CYP involved in drug metabolism is determined by the chemical structure of the drug. Moreover, the molecular species of CYP involved in metabolism varies with each site in the chemical structure, and there are also drugs that are metabolized by multiple molecular species of CYP.

When multiple drugs metabolized by the same molecular species of CYP compete for these metabolizing enzymes, the extent of competition varies with the affinity of the drug for the CYP, but it appears that metabolism is inhibited in some way. This results in drug interaction, such as an elevated blood concentrations, prolonged blood half-life, etc. Moreover, there are of course also drugs that are not metabolized, but have an inhibiting effect on specific molecular species of CYP.

Theophylline, caffeine, phenacetin, clomipramine, imipramine, fluvoxamine, zolpidem, clozapine, propranolol, propafenone, chlorzoxazone, tacrine, acetaminophen, ondansterone, verapamil, etc., are drugs that are metabolized by CYP1A2 and drugs that inhibit CYP1A2.

Diclofenac, naproxen, ibuprofen, piroxicam, flurbiprofen, indomethacin, phenytoin, carbamazepin, tolbutamide, glibenclamide, glipizide, glimepiride, warfarin, losartan, torsemide, dronabinol, tenoxicam, mefanamic acid, sulfafenazole, etc., are drugs that are metabolized by CYP2C9 and drugs that inhibit CYP2C9.

Mephenytoin, diazepam, phenytoin, phenobarbital, hexobarbital, mephobarbital, omeprazole, lansoprazole, proguanil, amitriptyline, clomipramine, imipramine, sitalopram, propranolol, thiridazine, carisoprodol, warfarin, nirvanol, etc., are drugs metabolized by CYP2C19 and drugs that inhibit CYP2C19.

Propafenone, flekainid, mexiletine, enkainid, spartein, N-propylazimalin, metoprolol, timolol, pindolol, propranolol, bufuralol, perbutolol, popindolol, alprenolol, carbedilol, debrisokin, indolamine, guanoxan, urapidil, nisergolin, risperidone, thioridazine, perphenazine, clozapine, trifluperiol, fluphenazine, chlorpromazine, haloperidol, clomipramine, nortriptyline, amitriptyline, imipramine, trimipramine, desipramine, zolpidem, brofalomin, amiframnine, paroxetine, fluoxetine, maprotiline, banrafaxin, fluvoxamin, trazadone, tomoxetin, dihydrocodeine, oxycodeine, codeine, tramadol, dextromethorphan, femformine, perhexelin, chlomiopran, quinidine, cimetidine, ondansteron, etc., are drugs that are metabolized by CYP2D6 and drugs that inhibit CYP2D6.

Anfentanyl, fentanyl, sulfentanyl, cocaine, dihydrocodeine, oxycodeine, tramadol, erythromycin, clarithromycin, troleandomycin, azithromycin, itraconazole, ketoconazole, dapsone, midazolam, triazolam, alprazolam, diazepam, zolpidem, felodipine, nifedipine, nitrendipine, amlodipine, isradipine, nicardipine, nimodipine, nisoldipine, nildipine, bepridil, diltiazem, verapamil, astemizole, terfenadine, loratidine, cyclosporine, tacrolimus, rapamycin, amiodarone, disopyramide, lidocaine, propafenone, quinidine, imipramine, amitriptyline, clomipramine, nafazodone, sertraline, trazodone, haloperidol, pimozide, carbamazepine, ethosuximide, trimethadione, simvastatin, lovastatin, fluvastatin, atrovastatin, etoposide, ifosfamide, paclitaxel, tamoxifen, taxol, vinblastine, vincristine, indinavir, ritonavir, saquinavir, testosterone, prednisolone, methylprednisolone, dexamethasone, proguanil, warfarin, finasteride, flutamide, ondansteron, zatosetron, cisapride, cortisol, zonisamide, desmethyldiazepam, conivaptan, etc., are drugs that are metabolized by CYP3A4 and drugs that inhibit CYP3A4 (Sogo Rinsho, 48(6), 1427–1431, 1999/Seishinka Chiryogaku, 14(9), 951–960, 1999).

Inhibition of metabolism resulting in elevation of blood concentration of midazolam and terfenadine, cyclosporine, etc., by erythromycin, methyl prednisolone by ketoconazole, and lovastatin by itraconazole are examples of drugs metabolized by CYP3A4 whose metabolism is inhibited by concomitant use.

Moreover, there are cases where foods that are metabolized by the same species of CYP as drugs compete for the same metabolizing enzymes to inhibit in some way the metabolism of these drugs. Moreover, there are also foods that inhibit a specific molecular species of CYP. For instance, various components contained in grapefruit juice inhibit CYP3A4 and therefore, interaction resulting in elevated blood concentrations of the drugs is seen when cyclosporine and tacrolimus, midazolam, triazolam, terfenadine, etc., which are metabolized by CYP3A4, are taken with grapefruit juice.

On the other hand, it is known that there are drugs that induce drug-metabolizing enzymes. For instance, rifampicin induces CYP3A4, CYP2C9 and CYP2C19 to promote metabolism of nifedipine, warfarin, diazepam, cyclosporine, disopyramide, torbutamide, ethinyl estradiol, etc., and reduce blood concentrations.

(b) Interaction in terms of drug absorption

The route of absorption of drugs is also by the skin or oral mucosa, etc., but the main route of absorption is by the digestive tract.

Changes in gastric pH due to the effect of other drugs used concomitantly changes solubility of drugs and controls or promotes absorption from the digestive tract. For instance, gastric pH rises to 3 to 5 with administration of cimetidine during concomitant use of cimetidine and ketoconazole and as a result, there is a reduction in solubility of ketoconazole and absorption via the digestive tract is inhibited, leading to a reduction in the blood concentration.

There are cases where when a drug is actively absorbed with concomitant drugs via the same carriers on the epithelial cells of the small intestines, absorption of the concomitant drugs is inhibited by this drug. For instance, it is reported that there is a reduction by approximately half in the cefadroxil plasma concentration when cefadroxil, a betalactam antibiotic, is concomitantly administered with cefalexine. This reduction in the blood concentration is apparently due to inhibition as a result of competition for the carrier by the two drugs.

(c) Interaction in terms of drug distribution

Drugs that have been absorbed via the digestive tract or have moved to the blood from the site of administration are distributed to blood cells at a specific ratio, or bind with proteins in plasma. The free fraction of the drug is distributed to each tissue to realize pharmacological action and therefore, when drug bound to protein is expelled from this binding site and interaction occurs so that the concentration of the free fraction of the drug rises, this pharmacological effect is enhanced. For instance, warfarin, torbutamide, etc., are released from the protein binding site, resulting in a rise in the concentration of the free fraction of the drug, when they are concomitantly used with aspirin, etc.

Moreover, P glycoproteins are found in the cells of the mucosa of the small intestines, cells of the uriniferous tubules, and endothelial cells of the capillaries of the brain, and they have the mechanism of transporting many drugs to outside the cells. When a drug that inhibits P glycoprotein is concomitantly used with a drug that is transported via P glycoprotein, there are cases where secretion of drugs into the intestines, transporting drugs out of the brain, and excretion in urine are inhibited. Vinblastin, vincristin, doxorubicin, etoposide, taxol, adriamycin, dexamethasone, hydrocortisone, verapamil, diltiazem, nifedipine, nicardipine, cyclosprin, tacrolimus, acebutolol, metoprolol, nadolol, timolol, prostaglandin, rodamine 123, digoxin, colchicine, dideoxyforscolin, etc., are drugs that are transported out by P glycoproteins. Etoposide, hydrocortisone, progesterone, testosterone, verapamil, diltiazem, nifedipine, felodipine, nitrendipine, nicardipine, cyclosporine, tacrolimus, amiodarone, lidocaine, quinidine, itraconazole, ketoconazole, erythromycin, tamoxifen, terfenadine, clorpromazine, selprolol, diprofloxacine, spironolactone are drugs that inhibit P glycoproteins ("Clinical Pharmacokinetics, Revised Version 2," Chapter II. Absorption of drugs from site of administration, page 19, Ryuichi Kato, author, Nankodo Publishers).

(d) Interaction in terms of excretion of drugs.

Drugs that have entered the body are excreted into the urine by the kidneys and are secreted and re-absorbed in the uriniferous tubules. Anionic carriers and cationic carriers participate in secretion from the uriniferous tubules. There is a possibility that drugs that use the same carrier will interact with one another. Probenecid, diodrast, acetazolamide, etc., are drugs that inhibit secretion via anionic carriers. Quinine, methyl nicotinamide, trazolin, tetramethyl ammonium, etc., are drugs that inhibit secretion via cationic carriers.

On the other hand, when re-absorption from the uriniferous tubules is inhibited, there is an increase in the amount excreted in urine and this lowers the blood concentration. For instance, re-absorption of chlorpropamide from the uriniferous tubules is inhibited by concomitant use with sodium bicarbonate.

A drug delivery system is defined as technology with which fate of drug molecules during the course of drug release, absorption, distribution, metabolism, and excretion is precisely controlled in terms of time and space. Conventional drug delivery systems are used in order to selectively introduce drugs to the site where its effects will be manifested based on the desired concentration-time pattern and thereby obtain the best clinical results. Examples are targeting technology for increasing the therapeutic results of anticancer drugs and steroids at the targeted site while averting adverse reactions outside the targeted site and controlled release technology for reducing the number of administration time of hypotensive agent in 1 day or for avoiding adverse reactions. The use of the drug delivery system of the present invention is in no way intended to alleviate the adverse reactions involved with the drug itself, and it clearly is different from the use of conventional drug delivery systems in that its purpose is to avert undesirable drug interactions between the drug in question and concomitant drugs.

Of the drug delivery systems, technology for controlling release of drugs in particular is used in the present invention. Controlling the release of drugs is generally classified as (1) controlling the release time and (2) controlling the site of release, but there are also cases where the site of release is restricted as a result of controlling the release time and when the release time is delayed as a result of controlling the site of release. Moreover, there are cases in which there is merely a difference in which one of these is mainly controlled.

By means of the present invention, drug interaction between a drug and concomitant drugs is averted by either control by prolonging the drug release time by a certain time period or by controlling release of a drug specifically to a certain site in the digestive tract and as a result, staggering the time at which the drugs will reach the route of absorption, distribution, metabolism or excretion over which the drug competes with concomitant drugs. Consequently, the drug delivery system of the present invention includes cases where release of multiple drugs that are being used concomitantly is controlled, in addition to the case where release of only 1 drug is controlled.

Of the drug delivery systems of the present invention, timed-release control technology and technology for controlling release in the lower digestive tract are particularly effective and will be described below. However, the drug delivery system of the present invention is not particularly limited to these as long as the above-mentioned aversion of drug interaction can be achieved.

(1) Timed-release control technology

Timed-release control is technology with which the time until a drug begins to be released after it has been taken is prolonged for a certain time. This has the mechanism of initiating release of the drug in the preparation by extending the time when it comes into contact with the water content of the digestive tract and in further detail, technology of the following types have been developed (Gekkan Yakuji, 41(6), 35–38, 1999/Igaku no Ayumi, 178(8), 441–444, 1996).

① Insoluble membrane bursting-type

These are preparations where the drug and swelling agent are coated with a membrane that is insoluble in water. The water content penetrates the insoluble membrane to reach the inside, the inside swells, and the insoluble membrane at the surface bursts under pressure so that the drugs inside are exposed to outside liquid. The time until the water permeates and the inside swells so that the membrane ruptures determines the time when drug release begins. Examples are the TES (time-controlled explosion system) of Fujisawa Yakuhin Co., Ltd. (Pharm. Tech. Japan, 4, 1415–1422, 1988) and the prolonged release tablets of Tanabe Seiyaku (Chem. Pharm. Bull, 11, 3036–3041, 1992), whereby a core tablet made of swelling disintegrator is compressed into a tablet with a substance with low water permeability.

② Cap breakaway-type

This is an insoluble capsule filled with drug having a stopper made from a hydrophilic polymer. When water swells the hydrophilic plug and the cap can no longer remain in the opening in the capsule and flips off, the drug inside the capsule comes into contact with outside liquid and is released. The time until the cap flips off determines the time for which release of the drug is prolonged. The Pulsincap of Scherer DDS (Pharm. J., 247, 138, 1991), etc., are given.

③ Membrane permeation increasing-type

The preparation is drug and organic acid inside a resin layer comprising cationic groups. The water content penetrates the resin layer, the organic acid inside is dissolved, and the acid and cationic groups of the resin interact, resulting in an increase in penetrability of the resin and release of the drug. The granules of Tanabe Seiyaku (Maku 19, 392–399, 1994) comprising Eudragit RS as the outer layer and organic acid and drug as the inner layer, etc., are given.

④ Hydrogel layer dissolving-type

This is a preparation of drug encapsulated by hydrophilic polymer. The water content soaks into the hydrophilic polymer, the polymer gel is gradually dissolved, and the drug inside comes into contact with outside liquid and is released. The gel shape and gel dissolution determine the time for which release of the drug will be prolonged. The chronotropic DDS coated with a hydroxypropyl methyl cellulose layer of Milano University (Eur. J. Pharm. Biopharm, 40, 246–250, 1994) and tablets of Kumamoto University (Chem. Pharm. Bull., 43, 311–314, 1995) whereby hydroxyethyl cellulose is compressed into the core tablet containing drug are given as examples.

Furthermore, the applicant developed as an improved form a tablet with a core, which is obtained by compression molding a hydrophilic base and a hydrogel-forming polymer substance together with a core tablet containing drug. This preparation can be used as a drug delivery system for averting undesirable interaction between multiple drugs metabolized by the drug-metabolizing enzyme CYP3A4. This preparation preferably is a combination of a freely erodible filler mixed in the core tablet containing drug in order to completely dissolve or suspend the drug before drug release begins. (see, U.S. patent application Ser. No. 09/834, 410, filed on even date herewith, incorporated herein by reference in its entirety for all purposes). Malic acid, citric acid, polyethylene glycol, sucrose, etc., are given as examples of the freely erodible filler. A base that has a solubility of no more than 4 ml as the volume of water needed to dissolve 1 g of the base is preferred as the hydrophilic base, and water-soluble polymers such as polyethylene glycol, polyvinyl pyrrolidone, etc., sugar alcohols, such as D-sorbitol, xylitol, etc., saccharides, such as sucrose, maltose, lactulose, D-fructose, dextran, glucose, etc., surfactants, such as polyoxyethylene hydrogenated castor oil, polyoxyethylene polyoxypropylene glycol, polyoxyethylene sorbitan higher fatty acid esters, etc., salts, such as sodium chloride, magnesium chloride, etc., organic acids, such as citric acid, tartaric acid, etc., amino acids, such as glycine, β-alanine, lysine hydrochloride, etc., aminosaccharides, such as meglumine, etc., are given as examples. Polyethylene oxide, hydroxypropylmethyl cellulose, carboxymethyl cellulose sodium, hydroxyethyl cellulose, carboxyvinyl polymer, etc., are given as the hydrogel-forming polymer, and those with a high viscosity at the time of gelling or with a high viscosity-average molecular weight are preferred.

(2) Technology for controlling release in the lower digestive tract

Controlling release in the lower digestive tract is technology for controlling initial release of the drug until the preparation has reached the lower digestive tract, such as the ileum and/or colon, etc., after being taken. It has the mechanism of releasing the drug in the environment of the lower digestive tract.

The ileum and colon have more bacteria than the stomach or upper small intestine and therefore, by coating the drug with a polymer that is decomposed by bacterial enzymes, the drug is not released in the stomach or upper small intestines. The polymer at the preparation surface is decomposed and dissolved and the drug is released after reaching the ileum and/or colon. Systems whereby azo aromatic polymers are decomposed by the azo reductase of intestinal flora of the University of Ohio (Science 233, 1081, 1986) and the University of Utah (Pharmaceutical Research, 9(12), 1540–1545, 1992), systems whereby polysaccharides are decomposed by the β-galactosidase of intestinal flora of Freiburg University (Pharmaceutical Research 10(10), S218, 1993), and systems of decomposition by chitosanase using chitosan of Teikoku Seikayu (Japanese Patent No. Hei 4(1992)-217924) are given. A system that uses a lectin-type substance present in the large intestines of the University of Utah (Proc. Int. Symp. Control. Rel. Bioact. Mat., 17, 130–131, 1990) is also reported.

Furthermore, there is also the system of the applicants (International Disclosure No. 95/28963) whereby organic acid is generated using intestinal bacteria and as a result, the film covering the drug is dissolved by said organic acid without affecting pH of the nearby cecum and the drug is specifically released to a site in the colon. In concrete terms, it is a system for specific release of drug in the colon of the digestive tract consisting of drug that is coated with a polymer that is dissolved by an organic acid and a saccharide that quickly generates an organic acid as a result of reaction with intestinal flora in the lower digestive tract.

The drug preparation for averting drug interaction of the present invention can be prepared by conventional methods as an oral solid preparation, an oral liquid preparation, or an injection using the above-mentioned timed-release technology and/or technology for controlling the site of release and an organic or inorganic carriers, filler, and other additives appropriate for oral or non-oral administration. The drug preparation of the present invention is preferably an oral drug preparation.

A system for averting drug interaction that uses the drug delivery system of the present invention will now be explained based on the type of drug interaction.

(a) System for averting interaction in terms of drug metabolism

In general, when multiple drugs that are metabolized by a drug-metabolizing enzyme of the same molecular species compete for a metabolizing enzyme in the liver, metabolism of the drug that has inferior affinity for the metabolizing enzyme is inhibited and interaction in the form of a rise in the blood concentration and prolonged blood half life is seen. In addition, when a drug that is metabolized by a certain drug-metabolizing enzyme and a drug that interferes with the same metabolizing enzyme are both present in the liver, metabolism is inhibited and interaction in the form of a rise in the blood concentration and prolonged blood half life is seen. Consequently, competition with concomitant drugs over a drug-metabolizing enzyme can be averted by controlling the release time so that a drug will reach the drug-metabolizing enzyme in the liver a specific time after a concomitant drug has been absorbed. Moreover, competition over a drug-metabolizing enzyme can be averted by releasing a drug specifically in the lower digestive tract and thereby staggering the time when concomitant drugs reach the liver.

In addition, CYP3A4 accounts for more than half of drug metabolism by CYP and as much as 80% of the amount distributed to the liver is also distributed to upper small intestines consisting of the duodenum and jejunum. Therefore, when a drug metabolized by CYP3A4 is orally administered, it is metabolized at the epithelium of the small intestines before it is absorbed from the digestive tract. Consequently, competition over CYP3A4 in the upper small intestines can be averted by (1) delaying the drug release time using timed-release control technology, which should avert coexistence of at the site of metabolism of concomitant drugs (epithelium of the small intestines and liver) or (2) by releasing the drug in the ileum and colon in which little CYP3A4 is distributed using technology for controlling release specifically in the lower digestive tract.

For instance, inhibition of midazolam metabolism due to competition with conivaptan and the rise in the blood concentration that accompanies the same can be averted by administration with a timed-release preparation with which release of the conivaptan in the digestive tract is delayed by as much as 2 hours, as shown in the examples and test examples given later.

(b) System for averting interaction in terms of drug absorption

Interaction involving absorption of drugs occurs mainly in the digestive tract with oral administration and is the result of an effect on solubility and permeability of the intestinal epithelium due to a change in gastric pH. In concrete terms, drug interaction can be averted by (1) timed-release control whereby a drug reaches the site of the digestive tract in question once absorption of concomitant drugs from the digestive tract has been completed or (2) by technology for controlling the site of release site whereby the site in the digestive tract at which concomitant drugs are absorbed is avoided.

For instance, a reduction in the plasma concentration of cefadroxil due to competition between cefadroxil and cephalexin over a carrier can be averted by administration with a timed-release preparation with which release of the cephalexin is delayed by as much as 3 hours.

(c) System for averting interaction in terms of drug distribution

Interaction involving drug distribution usually occurs with competition over a protein in the blood. Drug interaction in the blood can be averted by timed-release control or releasing a drug specifically in the lower digestive tract so that it reaches the blood after the blood concentration of concomitant drugs has dropped to a certain point.

For instance, inhibition of binding of acetohexamide with blood proteins induced by aspirin and a rise in the free acetohexamide concentration of the blood and hypoglycemic symptoms that accompany the same can be averted by controlling liberation of acetohexamide from blood proteins as a result of administration of aspirin with a timed-release preparation with which release in the digestive tract is delayed by as much as 4 hours after oral administration.

(d) System for averting interaction in terms of drug excretion

Interaction involving drug excretion often occurs due to competition over a carrier in the uriniferous tubules. Interaction in the uriniferous tubules can be averted by timed-release control or release of a drug specifically to the lower digestive tract so that a drug reaches the kidneys once excretion of concomitant drugs from the uriniferous tubules has been completed for the most part.

For instance, a reduction in renal excretion as a result of inhibition of secretion of procainamide via the uriniferous tubules induced by competition from cimetidine and an increase in the blood concentration that accompanies the same can be averted by oral administration with a timed-release preparation with which release of procainamide in the digestive tract is delayed by as much as 4 hours so that inhibition attributed to competition over secretion from the uriniferous tubules is controlled.

The system for averting drug interaction of the present invention can include other technology as long as the in vivo release time and/or release site of 1 or multiple drugs is controlled.

EXAMPLES

The present invention is described below in further details using examples and test examples, but the present invention is not limited to these examples, etc.

Conivaptan (which is used in the following examples, etc.) is easily obtained by or in accordance with the production method described in International Kokai Patent N. 95/03305, and Diltiazem, Ketoconazole, Rhodamine 123, Furosemide, Midazolam and Simvastatin are marked.

Example 1

Conivaptan Timed-release Preparation 1 part by weight conivaptan hydrochloride, 3 parts by weight HPMC2910, and 0.5 parts by weight polysorbate 80 were dissolved in 85.5 parts by weight dichloromethane-methanol mixture (8:2) and a solid dispersion was prepared by spray drying. Then 6 parts by weight malic acid were added to 9 parts by weight solid dispersion and mixed with a mortar and pestle. A core of 150 mg/tablet with a diameter of 6.5 mm was obtained under a compression force of 500 kg/punch using an oil press. Separatel, 62.5 mg polyethylene oxide (Polyox® WSR303) and 187.5 mg Macrogol 6000 were mixed with a mortar and pestle as the outer layer. The core was placed in the center of the outer layer and compression-coated tablets of the present invention of 400 mg (20 mg conivaptan)/tablet with a diameter of 9.5 mm were made under a compression force of 1,000 kg/punch using an oil press.

Example 2

Diltiazem Timed-release Preparation 50 parts by weight Macrogol 6000 were added to 100 parts by weight Diltiazem(Wako Junyaku Co., Ltd.) and mixed with a mortar and pestle. Then core tablets of 150 mg/tablet with a diameter of 7.0 mm were obtained under a compression force of 500 kg/punch using an oil press. 125 mg polyethylene oxide (Polyox® WSR303) and 175 mg Macrogol 6000 were separately mixed with a mortar and pestle to make the outer layer. The core tablet was placed in the center of the outer layer and compression-coated tablets of the present invention of 400 mg/tablet with a diameter of 10.0 mm were produced under a compression force of 1,000 kg/punch using an oil press.

Example 3

Ketoconazole Timed-release Preparation 100 parts by weight malic acid were added to 100 parts by weight Ketoconazole(Sigma) and mixed with a mortar and pestle. Then core tablet of 200 mg/tablet with a diameter of 8.0 mm were obtained under a compression force of 500 kg/punch using an oil press. 150 mg polyethylene oxide (Polyox® WSR303) and 180 mg Macrogol 6000 were separately mixed with a mortar and pestle to make the outer layer. The core tablet was placed in the center of the outer layer and compression-coated tablets of the present invention of 530 mg/tablet with a diameter of 11.0 mm were produced under a compression force of 1,000 kg/punch using an oil press.

Example 4

Conivaptan Timed-release Preparation 1 part by weight conivaptan hydrochloride, 3 parts by weight HPMC2910, and 0.5 parts by weight polysorbate 80 were dissolved in 85.5 parts by weight dichloromethane-methanol mixture(8:2) and a solid dispersion was prepared by spray drying. Then 8 parts by weight malic acid were added to 9 parts by weight of the solid dispersion and mixed with a mortar and pestle. Core tablets of 170 mg/tablet with a diameter of 8 mm were obtained under a compression force of 500 kg/punch using an oil press. 150 mg polyethylene oxide (Polyox® WSR303) and 180 mg Macrogol 6000 were separately mixed with a mortar and pestle to make the outer layer. The core tablet was placed in the center of the outer layer and compression-coated tablets of the present invention of 500 mg (20 mg conivaptan)/tablet with a diameter of 11 mm were produced under a compression force of 1,000 kg/punch using an oil press.

Example 5

Ketoconazole Timed-release Preparation 50 mg of citric acid were added to 100 mg of Ketoconazole and mixed with a mortar and pestle. Core of tablet with a diameter of 7.0 mm were obtained using an oil press. At the same time, 150 mg polyethylene oxide (Polyox® WSR303) and 100 mg Macrogol 6000 were mixed with a mortar and pestle as the outer layer. The core tablet was placed in the center of the outer layer and compression coated tablets of the present invention of 400 mg/tablet with a diameter of 10 mm were made under a compression force of 1,000 kg/punch using an oil press.

When Ketoconazole and Famotidine are co-administered orally, there is a decrease in solubility of Ketoconazole in line with the increase of gastric pH, and as a result there is a reduction in absorbability of Ketoconazole. The tablets obtained in the above were prepared for averting the reduction in the blood concentration of Ketoconazole by co-adiministration with Famotidine. When the tablet is orally administered, it begins to release Ketoconazole after a certain time in the lower small intestine and colon, and as a result, there is no effect on solubility of Ketoconazole depending on a change in gastric pH.

Example 6

Rhodamine 123 Timed-release Preparation

Nonpareil(trade name of spherical granules of sucrose, manufactured by Freund)(particle size: 710–840 m, 500 g) is entered and rolled in a centrifugal fluidized granulator (CF-36) EX, manufactured by Freund) and a mixture of Rhodamine 123(300 g) and fumaric acid (500 g) is gradually added thereto while spraying a solution of sucrose(240 g) in water-ethanol(3:1)(720 g), by which the ninpareil is surrounded and coated with the active substance and organic acid to give Rhodamine 123-containing granules. The Rhodamine 123 granules thus prepared(200 g) are entered into a fluidized bed coating machine(Flow Coater Mini, manufactured by Freund) and there is sprayed a coating liquid consisting of Eudragit RS30D (manufactured by Rohm Pharma, Germany)(168 g), talc(25 g), triethylcitrate(5 g) in water(234 g) with hot air-blowing of 60. Thereafter, the mixture is heat-treated at 60 to give controlled release Rhodamine 123-containing granules(280 g).

The obtained preparation was prepared for averting to promote translation into the brain of Verapamil(which is administered concomitantly) with inhibition of P glycoproteins by Rhodamine 123, because the release of Rhodamine 123 in the digestive tract is delayed by as much as 4 hours after oral administration.

Example 7

Furosemide Colon-delivery Preparation 200 mg of lactulose were added to 40 mg of Furosemide and mixed with a mortar and pestle. Core of tablet with a diameter of 7 mm were obtained under a compression force of 250 kg/punch using an oil press. The weight of the core tablet increased 20 mg after coating by ethanol-water solution (64:24(weight)) of Eudragit E/hydroxypropylmethylcellulose (4:1) and the weight increased 6.0 mg after coating by water-solution of hydroxypropylcellulose. The weight of the tablet increased 26 mg after coating by ethanol-water solution (17:1(weight)) of Eudragit L/talc/triethyl citrate (6:3:1).

The obtained preparation was prepared for averting delay of reduction of Furosemide in plasma caused by inhibition of secretion of Furosemide from the uriniferous tubules by concomitant drug Probenecid, because the tablets release Furocemide specifically in the colon.

Test Example 1

Dissolution Tests

Dissolution tests were conducted on the preparation in Example 1. The tests were conducted by the Second Dissolution Testing Method (Paddle Method) of the Pharmacopoeia of Japan (paddle rotation: 200 rpm) using 500 ml of 1st fluid of the Disintegration Testing Method of the Pharmacopoeia of Japan as the dissolution medium. Sampling was performed each hour and the conivaptan in the sampled solution was determined by the UV method.

(Results)

The results of the dissolution test are shown in FIG. 1. As is clear from the figure, it was confirmed that release of conivaptan started approximately 4 hours later with the timed-release preparation of Example 1.

Test Example 2

The following experiments were conducted using midazolam, which is metabolized CYP3A4, as a concomitant drug of conivaptan hydrochloride.

(Preparation of Sample Solution)

(1) Aqueous solution for oral administration containing midazolam: After preparing commercial midazolam injectable liquid (brand name: Dormicum® injection) to a concentration of 0.2 mg/ml with aqueous hydrochloric acid solution (pH of 3), HPMC2910 was added at 3-times the amount of midazolam to obtain a liquid for oral administration.

(2) Aqueous solution for oral administration containing conivaptan: Conivaptan hydrochloride was dissolved to a concentration of 0.5 mg/ml with an aqueous hydrochloric acid solution (pH of 3) to obtain a liquid for oral administration.

(Experiment 1)

Male beagle dogs (n=6) that had been fasted for approximately 20 hours were orally administered the aqueous solution for oral administration containing midazolam using a catheter for oral administration (4 mg/dog). After administration, blood was collected from the veins of the front legs and the plasma concentration of midazolam was determined by the HPLC/UV method over time.

(Experiment 2)

Male beagle dogs (n=6) that had been fasted for approximately 20 hours were orally administered the aqueous solution for oral administration containing conivaptan (10 mg/dog). Thirty minutes after administration the aqueous solution for oral administration containing midazolam was orally administered using a catheter for oral administration (4 mg/dog). After midazolam administration, blood was collected from the veins of the front legs and the plasma concentration of midazolam was determined by the HPLC/UV method over time.

(Experiment 3)

Male beagle dogs (n=6) that had been fasted for approximately 20 hours were orally administered the timed-release preparation of conivaptan of Example 1 (20 mg/dog) with 30 ml of water. Thirty minutes after administration an aqueous solution for oral administration containing midazolam (4 mg/dog) was orally administered using a catheter for oral administration. After midazolam administration, blood was collected from the veins of the front legs and the plasma concentration of midazolam was determined by the HPLC/UV method over time.

(Results)

The results are shown in the following table.

TABLE 1

AUC of midazolam plasma concentration

|  | AUC (ng.h/ml) |
| --- | --- |
| Experiment 1 (midazolam singular administration) | 9.0 ± 6.0 |
| Experiment 2 (midazolam + aqueous conivaptan solution) | 21.2 ± 8.5* |
| Experiment 3 (midazolam + conivaptan timed-release preparation) | 10.9 ± 7.3 |

*p < 0.05 (to Experiment 1)

As is clear from the results from Experiment 1 and Experiment 2, when the aqueous solution for oral administration containing conivaptan was concomitantly used by oral administration before oral administration of midazolam, significant changes were seen in that there was significant elevation of the midazolam blood concentration and the area under concentration(AUC) curve increased by at least 2-fold, etc., when compared to singular oral administration of midazolam(Table 1). The reason for this apparently is conivaptan, which has the same route of metabolism by CYP3A4 inhibits metabolism of midazolam in the small intestines and as a result, there is an increase in the midazolam blood concentration and the AUC.

On the other hand, as is clear from the results of Experiment 1 and Experiment 3, when the preparation of Example 1 was concomitantly used by oral administration before oral administration of the midazolam, the midazolam blood concentration and AUC showed almost the same results as with midazolam singular administration (Table 1). From this finding it appears that by means of the preparation of the present invention, metabolism of the midazolam by CYP3A4 in the small intestine is not inhibited by conivaptan because conivaptan is released after the midazolam has been metabolized by CYP3A4 in the upper small intestine and as a result, there is no effect on the metabolism blood concentration or AUC. Moreover, it was confirmed that the blood concentration of conivaptan was enough to provide pharmacologically the therapeutic or prophylactic effect of conivaptan once the midazolam had cleared from the blood.

Test Example 3

The following experiments were performed using Diltiazem, which inhibits metabolism by CYP3A4, and Midazolam, which is metabolized by CYP3A4.

(Preparation of Sample Solution)

(1) Aqueous solution for oral administration containing midazolam: After preparing commercial midazolam injectable liquid (brand name: Dormicum® injection) to a concentration of 0.2 mg/ml with aqueous hydrochloric acid solution (pH of 3), HPMC2910 was added at 3-times the amount of midazolam to obtain a liquid for oral administration.

(2) Aqueous solution for oral administration containing diltiazem: Diltiazem was dissolved to a concentration of 20 mg/ml to obtain a liquid for oral administration.

(Experiment 4)

The aqueous solution for oral administration containing midazolam was orally administered (4 mg/dog) using a catheter for oral administration to a male beagle dogs (n=3) that had been fasted for approximately 20 hours. After administration, blood was collected from the veins of the front limbs of the dogs and the midazolam concentration of the plasma was determined by the HPLC/UV method.

(Experiment 5)

The aqueous solution for oral administration containing diltiazem was orally administered (200 mg/dog) using a catheter for oral administration, while at the same time, the aqueous solution for oral administration of midazolam was orally administered (4 mg/dog) using a catheter for oral administration to male beagle dogs(n=3) that had been fasted for approximately 20 hours. After administration, blood was collected from the veins of the front limbs of the dogs and the midazolam concentration of the plasma was determined by the HPLC/UV method.

(Experiment 6)

The pharmaceutical preparation of Example 2 was orally administered (200 mg/dog) with 30 ml of water using a catheter for oral administration, while at the same time, the aqueous solution for oral administration of midazolam was orally administered (4 mg/dog) using a catheter for oral administration to male beagle dogs(n=3) that had been fasted for approximately 20 hours. After administration, blood was collected from the veins of the front limbs of the dogs and the midazolam concentration of the plasma was determined by the HPLC/UV method.

(Results)

The results are shown in the following table.

TABLE 2

Mean AUC of midazolam plasma concentration

|  | AUC (ng.h/ml) |
|---|---|
| Experiment 4 (midazolam singular administration) | 55.0 |
| Experiment 5 (midazolam + aqueous diltiazem solution) | 162.6 |
| Experiment 6 (midazolam + diltiazem timed-release preparation) | 48.9 |

As is clear from the results from Experiment 4 and Experiment 5, when the aqueous solution for oral administration containing diltiazem was concomitantly used by oral administration simultaneously with midazolam oral administration, there was a marked rise in the blood concentration of midazolam and the average area under concentration(AUC) increased by as much as 3-times (Table 2) when compared to midazolam singular administration. The reason for this apparently that diltiazem inhibits metabolism by CYP3A4 and as a result, induces an increase in the midazolam AUC.

On the other hand, as is clear from Experiment 4 and Experiment 6, almost the same results as with midazolam singular administration are seen in terms of the midazolam AUC when the pharmaceutical preparation of Example 2 was concomitantly used by oral administration simultaneously with midazolam oral administration (Table 2). Thus, it appears that the pharmaceutical preparation of the present invention diltiazem is released after midazolam has been metabolized by CYP3A4 in the upper small intestine and therefore had no effect on the AUC of midazolam.

Test Example 4

The following experiments were conducted using Ketoconazole, which inhibits metabolism by CYP3A4 and Midazolam, which is metabolized by CYP3A4.

(Preparation of Sample Solution)

(1) Aqueous solution for oral administration containing midazolam: After preparing commercial midazolam injectable liquid (brand name: Dormicum® injection) to a concentration of 0.2 mg/ml with aqueous hydrochloric acid solution (pH of 3), HPMC2910 was added at 3-times the amount of midazolam to obtain a liquid for oral administration.

(2) Aqueous solution for oral administration containing ketoconazole: Ketoconazole was dissolved to a concentration of 5 mg/ml to obtain a liquid for oral administration.

(Experiment 7)

The aqueous solution for oral administration containing midazolam was orally administered(4 mg/dog) using a catheter for oral administration to male beagle dogs (n=2) that had been fasted for approximately 20 hours. After administration, blood was collected from the veins of the front limbs of the dogs and the midazolam concentration of the plasma was determined by the HPLC/UV method.

(Experiment 8)

The aqueous solution for oral administration containing ketoconazole was orally administered(100 mg/dog) using a catheter for oral administration, while at the same time, the aqueous solution for oral administration of midazolam was orally administered(4 mg/dog) using a catheter for oral administration to male beagle dogs (n=2) that had been fasted for approximately 20 hours. After administration, blood was collected from the veins of the front limbs of the dogs and the midazolam concentration of the plasma was determined by the HPLC/UV method.

(Experiment 9)

The pharmaceutical preparation of Example 3 was orally administered(200 mg/dog) with 30 ml of water using a catheter for oral administration, while at the same time, the aqueous solution for oral administration of midazolam was orally administered (4 mg/dog) using a catheter for oral administration to male beagle dogs (n=2) that had been fasted for approximately 20 hours. After administration, blood was collected from the veins of the front limbs of the dogs and the midazolam concentration of the plasma was determined by the HPLC/UV method.

(Results)

The results are shown in the following table.

TABLE 3

Mean AUC of midazolam plasma concentration

|  | AUC (ng.h/ml) |
|---|---|
| Experiment 7 (midazolam singular administration) | 68.7 |
| Experiment 8 (midazolam + aqueous ketoconazole solution) | 245.5 |
| Experiment 9 (midazolam + ketoconazole timed-release preparation) | 69.5 |

As is clear from the results from Experiment 7 and Experiment 8, when the aqueous solution for oral administration containing ketoconazole was concomitantly used by oral administration before midazolam oral administration, there was a marked rise in the blood concentration of midazolam and the average area under concentration (AUC) increased by as much as 4-times (Table 3) when compared to midazolam singular oral administration. The reason for this is apparently that ketoconazole inhibits metabolism by CYP3A4 and as a result, induces an increase in the midazolam AUC.

On the other hand, as is clear from the results of Experiment 7 and Experiment 9, when the pharmaceutical preparation of Example 3 was concomitantly used by oral administration simultaneously with midazolam oral concentration, the midazolam AUC showed approximately the same result as with midazolam singular administration (Table 3). Thus, it appears that the pharmaceutical preparation of the present invention, ketoconazole is released after the midazolam has been metabolized by CYP3A4 in the upper small intestine and therefore had no effect on the AUC of midazolam.

Test Example 5

The following experiments were conducted using Conivaptan which impairs metabolism by CYP3A4 and Simvastatin which is metabolized by CYP3A4.

(Preparation of Sample Solution)

(1) Aqueous solution for oral administration containing conivaptan: PEG200 5 mM, phosphatidic acid and conivaptan hydrochloride was mixed at the rate of 1:1:8 and prepared to a concentration of 1.67 mg/ml to obtain a liquid for oral administration.

(2) Preparation for oral administration containing simvastatin: Commercial Lipovas tablet (Banyu seiyaku) was used.

(Experiment 10)

Simvastatin pharmaceutical preparation for oral administration was orally administered (25 mg/monkey) to male cynomologous monkeys(n=6) that had been fasted for approximately 12 hours on Test Day 1. Blood was collected from the femoral vein over time following administration and the simvastatin concentration of plasma was determined by the LC/MS/MS method. An aqueous solution for oral administration containing conivaptan was orally administered (5 mg/monkey) using a nasogastric tube to male cynomologous monkeys(n=6) that had been fasted for approximately 12 hours or longer each morning from Test Day 2 up to Test Day 6. Simvastatin pharmaceutical preparation for oral administration was orally administered (25 mg/monkey) simultaneously with oral administration of the aqueous solution for oral administration containing conivaptan on Test Day 6. Blood was collected from the femoral vein over time following administration and the simvastatin concentration of plasma was determined by the HPLC/UV method.

(Experiment 11)

Simvastatin pharmaceutical preparation for oral administration was orally administered (25 mg/monkey) to male cynomologous monkeys(n=6) that had been fasted for approximately 12 hours on Test Day 1. Blood was collected from the femoral vein over time once administration was completed and the simvastatin concentration of plasma was determined by the LC/MS/MS method. The pharmaceutical preparation of Example 4 was orally administered (20 mg/monkey) to male cynomologous monkeys(n=6) that had been fasted for approximately 12 hours or longer each morning from Test Day 2 up to Test Day 6. On Test Day 6, simvastatin pharmaceutical preparation for oral administration was orally administered (25 mg/monkey) simultaneously with oral administration of the pharmaceutical preparation of Example 4. Blood was collected from the femoral vein over time once administration was completed and the simvastatin concentration of plasma was determined by the HPLC/UV method.

(Results)

The results are shown in the following table.

TABLE 4

Mean AUC of simvastatin plasma concentration

| Experiment | AUC (ng.h/ml) Average | rate of AUC Test Day 1/ Test Day 6 Average |
|---|---|---|
| 10 conivaptan single administration (Test Day 1) | 62.7 | X 24.1 |
| aqueous conivaptan solution co-administration (Test Day 6) | 806.5 | (54.1–5.8) |
| 11 conivaptan single administration (Test Day 1) | 65.2 | X 4.1 |
| preparation of Example 4 co-administration (Test Day 6) | 324.3 | (7.4–0.2) |

As is clear from the results of Experiment 10 and Experiment 11, there were marked changes when simvastatin pharmaceutical preparation for oral administration was concomitantly used by oral administration simultaneously after continuous administration of the aqueous solution for oral administration of conivaptan in that the simvastatin concentration in blood rose markedly and the AUC was approximately 24-times or more that of singular administration, etc., when compared to simvastatin singular oral administration (Table 4). The reason for this is apparently that conivaptan impairs metabolism by CYP3A4 and as a result, induces an increase in the simvastatin AUC.

On the other hand, as is clear from the results of Experiment 10 and Experiment 11, when the pharmaceutical preparation of Example 4 was concomitantly used by oral administration simultaneously with simvastatin pharmaceutical preparation for oral administration after being continuously administered, the simvastatin AUC was 4-times higher when compared to simvastatin singular administration and was very low when compared to concomitant use with the aqueous solution for oral administration of conivaptan(Table 3). Thus, it appears that the pharmaceutical preparation of the present invention, conivaptan hydrochloride is released after simvastatin has been metabolized by CYP3A4 in the upper small intestine and therefore, a rise in the simvastatin AUC can be controlled.

Based on the above-mentioned, it was confirmed that the undesirable effects on the blood concentration of concomitant drug(s) by a drug when the drug and the concomitant drug(s) are metabolized by the drug-metabolizing enzyme CYP3A4, can be averted with the drug delivery system that uses timed-release control of the present invention.

INDUSTRIAL APPLICABILITY

Undesirable pharmacokinetic drug interaction that occurs with concomitant use of multiple drugs can be averted using the system for averting drug interaction of the present invention. Consequently, novel treatment by a combination of drugs that could not be concomitantly used in the past is possible. Furthermore, drug products can be developed and novel drug products can be presented from drugs that were impossible to develop in the past because of drug interaction when used concomitantly with other drugs, regardless of their excellent pharmacological effects and lack of problems with adverse reactions.

In addition, it is possible to avert undesirable pharmacokinetic adverse reactions when a drug has been taken with a specific food with the system for averting drug interaction of the present invention. Consequently, patient compliance will be improved because the precautions for use explained to the patient by a pharmacist will be reduced.

What is claimed is:

1. A system for averting undesirable drug interaction between a drug and concomitant drug(s), both of which are metabolized by the same molecular species of drug-metabolizing enzyme in humans, or between a drug and concomitant drug(s) that is metabolized by the molecular species of drug-metabolizing enzymes that is inhibited by the said drug, which comprises timed-release control of the said drug or control of the site of release of the said drug to the digestive tract.

2. A system for averting undesirable drug interaction between a drug and concomitant drug(s), both of which metabolized by the drug metabolizing enzyme CYP3A4, or between a drug that inhibits CYP3A4 and concomitant drug(s) that is metabolized by CYP3A4, which comprises timed-release control of the said drug or controlling release specifically in the lower digestive tract of the said drug.

3. A drug preparation for averting undesirable drug interaction on the in vivo kinetics of a drug by concomitant drug(s) that inhibits in vivo metabolism of the said drug in humans, which comprises timed-release control of the concomitant drug or control of the site of release of the concomitant drug to the digestive tract.

4. A drug preparation for averting undesirable effects on the blood concentration of a drug by concomitant drug(s) that inhibits the in vivo metabolism of the said drug by CYP3A4 in humans, which comprises timed release control of the said drug or controlling release specifically in the lower digestive tract of the concomitant drug.

5. The drug preparation according to claim 4, whereby the said drug and the concomitant drug are a combination selected from anfentanyl, fentanyl, sulfentanyl, cocaine, dihydrocodeine, oxycodeine, tramadol, erythromycin, clarithromycin, troleandomycin, azithromycin, itraconazole, ketoconazole, dapsone, midazolam, triazolam, alprazolam, diazepam, zolpidem, felodipine, nifedipine, nitrendipine, amlodipine, isradipine, nicardipine, nimodipine, nisoldipine, nildipine, bepridil, diltiazem, verapamil, astemizole, terfenadine, loratidine, cyclosporine, tacrolimus, rapamycin, amiodarone, disopyramide, lidocaine, propafenone, quinidine, imipramine, amitriptyline, clomipramine, nafazodone, sertraline, trazodone, haloperidol, pimozide, carbamazepine, ethosuximide, trimethadione, simvastatin, lovastatin, fluvastatin, atrovastatin, etoposide, ifosfamide, paclitaxel, tamoxifen, taxol, vinblastine, vincristine, indinavir, ritonavir, saquinavir, testosterone, prednisolone, methylprednisolone, dexamethasone, proguanil, warfarin, finasteride, flutamide, ondansteron, zatsetrone, cisapride, cortisol, zonisamide, desmethyldiazepam, and conivaptan.

6. A method for averting undesirable drug-interaction on the in vivo kinetics of a drug by concomitant drug that inhibits the in vivo metabolism of the said drug by drug-metabolizing enzymes in humans, comprising administering to patients a drug preparation with which timed-release of the concomitant drug or release site of the concomitant drug to the digestive tract is controllable.

7. A method for averting undesirable effects on the blood concentration of a drug by concomitant drug that inhibits the in vivo metabolism of the said drug by CYP3A4, comprising administering to patients a drug preparation with which timed-release of the concomitant drug or release of the concomitant drug specifically to the lower digestive tract is controllable.

8. The method according to claim 7, whereby the said drug and the concomitant drug are a combination selected from anfentanyl, fentanyl, sulfentanyl, cocaine, dihydrocodeine, oxycodeine, tramadol, erythromycin, clarithromycin, troleandomycin, azithromycin, itraconazole, ketoconazole, dapsone, midazolam, triazolam, alprazolam, diazepam, zolpidem, felodipine, nifedipine, nitrendipine, amlodipine, isradipine, nicardipine, nimodipine, nisoldipine, nildipine, bepridil, diltiazem, verapamil, astemizole, terfenadine, loratidine, cyclosporine, tacrolimus, rapamycin, amiodarone, disopyramide, lidocaine, propafenone, quinidine, imipramine, amitriptyline, clomipramine, nafazodone, sertraline, trazodone, haloperidol, pimozide, carbamazepine, ethosuximide, trimethadione, simvastatin, lovastatin, fluvastatin, atrovastatin, etoposide, ifosfamide, paclitaxel, tamoxifen, taxol, vinblastine, vincristine, indinavir, ritonavir, saquinavir, testosterone, prednisolone, methylprednisolone, dexamethasone, proguanil, warfarin, finasteride, flutamide, ondansteron, zatsetrone, cisapride, cortisol, zonisamide, desmethyldiazepam, and conivaptan.

9. A drug preparation for averting undesirable effects on the blood concentration of a drug by concomitant drug(s) that inhibits the in vivo metabolism of the said drug by CYP3A4 in humans, which comprises timed release control of the said drug or controlling release specifically in the lower digestive tract of the concomitant drug, whereby:

the said drug and the concomitant drug are a combination selected from anfentanyl, fentanyl, sulfentanyl, cocaine, dihydrocodeine, oxycodeine, tramadol, erythromycin, clarithromycin, troleandomycin, azithromycin, itraconazole, ketoconazole, dapsone, midazolam, triazolam, alprazolam, diazepam, zolpidem, felodipine, nifedipine, nitrendipine, amlodipine, isradipine, nicardipine, nimodipine, nisoldipine, nildipine, bepridil, diltiazem, verapamil, astemizole, terfenadine, loratidine, cyclosporine, tacrolimus, rapamycin, amiodarone, disopyramide, lidocaine, propafenone, quinidine, imipramine, amitriptyline, clomipramine, nafazodone, sertraline, trazodone, haloperidol, pimozide, carbamazepine, ethosuximide, trimethadione, simvastatin, lovastatin, fluvastatin, atrovastatin, etoposide, ifosfamide, paclitaxel, tamoxifen, taxol, vinblastine, vincristine, indinavir, ritonavir, saquinavir, testosterone, prednisolone, methylprednisolone, dexamethasone, proguanil, warfarin, finasteride, flutamide, ondansteron, zatsetrone, cisapride, cortisol, zonisamide, desmethyldiazepam, and conivaptan.

10. A drug preparation for averting undesirable drug interaction on the in vivo kinetics of a drug by concomitant drug(s) that inhibits in vivo metabolism of the said drug in humans, which comprises timed-release control of the concomitant drug or control of the site of release of the concomitant drug to the digestive tract whereby:

the said drug and the concomitant drug are a combination selected from anfentanyl, fentanyl, sulfentanyl, cocaine, dihydrocodeine, oxycodeine, tramadol, erythromycin, clarithromycin, troleandomycin, azithromycin, itraconazole, ketoconazole, dapsone, midazolam, triazolam, alprazolam, diazepam, zolpidem, felodipine, nifedipine, nitrendipine, amlodipine, isradipine, nicardipine, nimodipine, nisoldipine, nildipine, bepridil, diltiazem, verapamil, astemizole, terfenadine, loratidine, cyclosporine, tacrolimus, rapamycin, amiodarone, disopyramide, lidocaine, propafenone, quinidine, imipramine, amitriptyline, clomipramine, nafazodone, sertraline, trazodone, haloperidol, pimozide, carbamazepine, ethosuximide, trimethadione, simvastatin, lovastatin, fluvastatin, atrovastatin, etoposide, ifosfamide, paclitaxel, tamoxifen, taxol, vinblastine, vincristine, indinavir, ritonavir, saquinavir, testosterone, prednisolone, methylprednisolone, dexamethasone, proguanil, warfarin, finasteride, flutamide, ondansteron, zatsetrone, cisapride, cortisol, zonisamide, desmethyldiazepam, and conivaptan.

11. The system for averting undesirable drug interaction of claim 1, wherein said drug and the concomitant drug are both metabolized by the same molecular species of drug-metabolizing enzyme in humans.

12. The system for averting undesirable drug interaction of claim 1, wherein the concomitant drug is metabolized by the molecular species of the drug-metabolizing enzymes that is inhibited by the said drug.

13. The system for averting undesirable drug interaction of claim 11, wherein said drug and the concomitant drug are both metabolized by CYP3A4.

14. The system for averting undesirable drug interaction of claim 12, the concomitant drug is metabolized by CYP3A4 and said drug inhibits CYP3A4.

15. The system for averting undesirable drug interaction between a drug and concomitant drug(s) of claim 1, wherein the timed-release control of the said drug is a member selected from the group consisting of insoluble membrane bursting-type, cap breakaway-type, membrane permeation increasing-type and hydrogel layer dissolving-type.

16. The system for averting undesirable drug interaction between a drug and concomitant drug(s) of claim 1, wherein control of the site of release of the said drug to the digestive tract is accomplished using a member selected from the group consisting of terms of drug metabolism, drug absorption, drug distribution, and drug excretion.

* * * * *